(12) United States Patent
Tseng et al.

(10) Patent No.: US 9,132,378 B2
(45) Date of Patent: Sep. 15, 2015

(54) PORTABLE OXYGEN GENERATOR

(71) Applicant: Li-Tek Electronics Technology Co., Ltd., Dongguan, Guangdong Province (CN)

(72) Inventors: Wenwei Tseng, Dongguan (CN); Jason Ouyang, Dongguan (CN); Bob Zhou, Dongguan (CN); Zuo Yang, Dongguan (CN); Guifeng Wei, Dongguan (CN)

(73) Assignee: LI-TEK ELECTRONICS TECHNOLOGY CO., LTD., Dongguan, Guangdong Province (CN)

( * ) Notice: Subject to any disclaimer, the term of this patent is extended or adjusted under 35 U.S.C. 154(b) by 0 days.

(21) Appl. No.: 14/079,722

(22) Filed: Nov. 14, 2013

(65) Prior Publication Data

US 2015/0128805 A1 May 14, 2015

(51) Int. Cl.
*B01D 53/02* (2006.01)
*B01D 53/047* (2006.01)
*A61M 16/10* (2006.01)

(52) U.S. Cl.
CPC ............. *B01D 53/047* (2013.01); *A61M 16/10* (2013.01)

(58) Field of Classification Search
CPC ............................... B01D 53/047; A61M 16/10
See application file for complete search history.

(56) References Cited

U.S. PATENT DOCUMENTS

| 7,066,985 | B2 * | 6/2006 | Deane et al. | 95/96 |
| 7,438,745 | B2 * | 10/2008 | Deane et al. | 95/96 |
| 2005/0072423 | A1 * | 4/2005 | Deane et al. | 128/202.26 |
| 2005/0103341 | A1 * | 5/2005 | Deane et al. | 128/204.26 |
| 2011/0030684 | A1 * | 2/2011 | Wilkinson et al. | 128/204.18 |
| 2012/0055340 | A1 * | 3/2012 | Wilkinson et al. | 96/115 |

* cited by examiner

*Primary Examiner* — Christopher P Jones
(74) *Attorney, Agent, or Firm* — Jackson IPG PLLC; Demian K. Jackson

(57) ABSTRACT

A portable oxygen generator comprises an air pump, a molecular tube and a molecular seat, the molecular tube is detachably fixed on the side wall of the molecular seat, the air pump is disposed at the lower part of the molecular seat. An air filter bucket, an oxygen storage bucket and an exhaust silencing bucket are disposed inside the molecular seat, the air filter bucket is provided with an air inlet communicated with the outside air. An air channel, an oxygen channel and an exhaust channel are disposed inside the molecular seat, the air channel is respectively communicated with the air filter bucket, the air pump and the molecular tube, the oxygen channel is respectively communicated with the molecular tube and the oxygen storage bucket, the exhaust channel is respectively communicated with the molecular tube and the exhaust silencing bucket, the air channel, the oxygen channel and the exhaust channel are respectively connected with a solenoid valve.

14 Claims, 6 Drawing Sheets

PORTABLE OXYGEN GENERATOR

FIELD OF THE INVENTION

The invention relates to the technical field of oxygen generation equipment, in particular to a portable oxygen generator.

BACKGROUND OF THE INVENTION

With the development of social civilization and medical technology, researches and controls on diseases are improved prominently, so the life expectancy of human beings increases. As a result, the coming of aging society has become an inevitable trend. However, relatively speaking, this will also cause many negative effects, of which the heavy damage to the global environment is most obvious. For example, sometimes human beings will surfer the counterattack of unknown diseases (for example, SARS) or severe environment (for example, rainstorm or bitter cold, intense heat or earth flow). Nowadays, the external environment is worrying. To reduce the invasion possibility of increasingly severe environment and unknown diseases, human being should make various preparations. As oxygen is an indispensable gas for human existence, an oxygen generator, into which molecular sieve material is filled and high pressure air is imported to generate and then export oxygen itself, becomes an important device.

Besides for emergency, the oxygen generator is often used in symptoms of many chronic diseases. For example, it is necessary for asthmatics and patients with breathing difficulties to prepare an oxygen generator in reserve at any time. In addition, more pure oxygen may promote the blood circulation, make the brain clear, remove fatigue and effectively improve the working efficiency; therefore, no matter in daily life or workplaces, preparation of an oxygen generator to be ready to use at any time is also a healthy lifestyle.

However, as the majority of the existing oxygen generators are assembled from ready-made components and have complicated airflow conduits outside, the existing oxygen generators has incompact and huge assembly space. It is inconvenient for carrying or transportation. Even the whole cost is influenced so that the price of the existing oxygen generators is still high.

SUMMARY OF THE INVENTION

In view of the deficiencies in the prior art, an object of the invention is to provide a portable oxygen generator with simple structure, compact assembly space, convenience for carrying or transportation and low cost.

To achieve the above purpose, the following technical solution is employed in the invention.

A portable oxygen generator is provided, comprising an air pump and a molecular tube, further comprising a molecular seat, the molecular tube being detachably fixed on the side wall of the molecular seat, the air pump being disposed at the lower part of the molecular seat; an air filter bucket, an oxygen storage bucket and an exhaust silencing bucket are disposed inside the molecular seat, the air filter bucket being provided with an air inlet communicated with the outside air; an air channel, an oxygen channel and an exhaust channel are disposed inside the molecular seat, the air channel being respectively communicated with the air filter bucket, the air pump and the molecular tube, the oxygen channel being respectively communicated with the molecular tube and the oxygen storage bucket, the exhaust channel being respectively communicated with the molecular tube and the exhaust silencing bucket, the air channel, the oxygen channel and the exhaust channel being respectively connected with a solenoid valve.

Wherein, the molecular tube comprises a first molecular tube and a second molecular tube, the first molecular tube and the second molecular tube being communicated with each other through an oxygen complementation channel, the oxygen complementation channel being connected with a solenoid valve, oxygen complementation control valves being respectively disposed on two sides of the solenoid valve.

Wherein, the molecular seat comprises an upper cover, a seat body and a lower cover, which are disposed in turn from top to bottom, the seat body being respectively connected with the upper cover and the lower cover by bolts.

Wherein, an oxygen outlet tip is disposed at the air outlet end of the molecular tube, and a groove for the oxygen outlet tip fitted with the oxygen outlet tip in mounting is disposed on the upper cover.

Wherein, an umbrella-shaped non-return reflux device is disposed on the top of the oxygen outlet tip.

Wherein, the seat body comprises a top, a middle part and a bottom, which are integrated together, a side face of the seat body being I-shaped, through holes being respectively disposed at two ends of the top, counter bores being respectively disposed at two ends of the bottom, the counter bores being right below the through holes.

Wherein, a motor connector is disposed at the air outlet end of the air pump, a concave-convex slot joint is disposed in a position where the lower cover directly faces the air inlet end of the molecular tube, and the concave-convex slot joint is connected with the motor in a way of muff-coupling.

Wherein, multiple cooling fins, arrayed at intervals, are disposed on the outer wall of the molecular seat.

Wherein, the air channel between the molecular tube and the air pump is connected with an over-pressure protection device.

Wherein, an air suction tip is disposed at the air inlet end of the air pump, a suction silencing channel is disposed between an air cylinder and an air reservoir of the air pump, and the rotating shaft of the air pump is provided with a safety cover.

The beneficial effects of the invention are as follows: when in service, the outside air enters the air pump via the air filter bucket and the air channel in the molecular seat. The air is compressed by the air pump and then pumped into the molecular tube. After the molecular tube feeds air and generates oxygen, the oxygen is stored in the oxygen storage bucket via the oxygen channel, and the rest of nitrogen is output to the exhaust silencing bucket via the exhaust channel. In the portable oxygen generator disclosed by the invention, the external pipelines and the air pipelines are centralized inside the molecular seat, so no air pipelines can be seen from the appearance; the assembly space is compact, this is convenient for carrying or transportation; and the production cost is greatly reduced, thus the widespread popularization and application are benefited.

The advantages of the invention are as follows:

(1) In the oxygen generator disclosed by the invention, a high-tech integrated pipeline airflow loop type space is designed, so it breaks through the structure of complicated airflow conduits outside of a traditional oxygen generator, and it is convenient for assembling, carrying or transportation.

(2) The invention has simple structure, and the design of two molecular tubes may realize cyclic oxygen generation with high working efficiency.

(3) The arrangement of a plurality of solenoid valves is advantageous to coordinate with all gas channels in the molecular seat to realize conditioned open or closed communication, with simple operation and high processing efficiency.

(4) The oxygen generator disclosed by the invention has light and handy size and convenience for carrying, and is applicable for family healthcare oxygen therapy, oxygen supplementation after physical exercise, etc. Meanwhile, the oxygen generator may be applied in severe environment with highland, high altitude, rarefied air, etc.

DETAILED DESCRIPTION OF THE INVENTION

Figure 1:
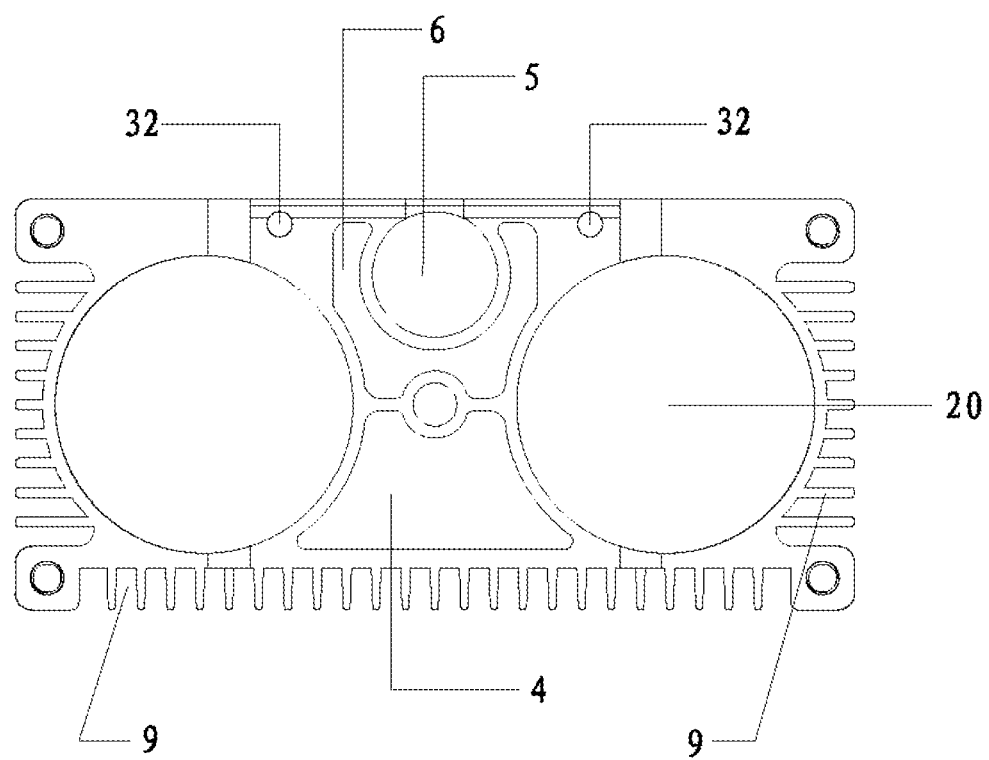
FIG. 1 is a plane structure diagram of a seat body of a molecular seat of a portable oxygen generator in the invention.

The invention will be further described as below with reference to drawings.

As shown in FIG. 1 to FIG. 6, a portable oxygen generator of the invention comprises an air pump 1 and a molecular tube 2, and further comprises a molecular seat 3. The molecular tube 2 is detachably fixed on the side wall of the molecular seat 3. The air pump 1 is disposed at the lower part of the molecular seat 3. An air filter bucket 4, an oxygen storage bucket 5 and an exhaust silencing bucket 6 are disposed inside the molecular seat 3. The air filter bucket is provided with an air inlet communicated with the outside air. An air channel 31, an oxygen channel 32 and an exhaust channel 33 are disposed inside the molecular seat 3. The air channel 31 is communicated with the air filter bucket 4, the air pump 1 and the molecular tube 2, respectively. The oxygen channel 32 is communicated with the molecular tube 2 and the oxygen storage bucket 5, respectively. The exhaust channel 33 is communicated with the molecular tube 2 and the exhaust silencing bucket 6, respectively. The air channel 31, the oxygen channel 32 and the exhaust channel 33 are connected with a solenoid valve 7, respectively.

When in service, the outside air is filtered and cleaned by the air filter bucket 4 inside the molecular seat 3, and then conveyed to the air pump 1 via the air channel 31. The air pump 1 conveys the compressed air into the molecular tube 2. A conversion solenoid valve is employed to control the air channel 31 at the lower part of the molecular tube 2 to feed and exhaust air in turn. Under the action of the molecular sieve material, the molecular tube 2 produces oxygen. The generated oxygen is stored in the oxygen storage bucket 5 via the oxygen channel 32, and the surplus nitrogen is output to the exhaust silencing bucket 6 via the exhaust channel 33. Oxygen may be output from the oxygen storage bucket 5 when a user needs oxygen. In the portable oxygen generator disclosed by the invention, the external pipelines and the air pipelines are centralized inside the molecular seat 3, so no air pipelines can be seen from the appearance; the assembly space is compact, this is convenient for carrying or transportation; and the production cost is greatly reduced, thus the widespread popularization and application are benefited. The molecular tube (i.e., molecular sieve tube) in the invention generates oxygen in a way of PSA (Pressure Swing Adsorption) oxygen generation, wherein the PSA oxygen generation technology belongs to the prior art, and the oxygen generation principle thereof will not be described again here.

Specifically, on the side wall of the molecular seat 3, a molecular tube groove 20 is provided for fixing the molecular tube 2. The mounting of the molecular tube 2 is convenient due to such a simple structure. The air outlet end of the oxygen storage bucket 5 is connected with an oxygen supply pipeline 52. The air inlet end of the oxygen supply pipeline 52 is in turn connected with an oxygen output quantity control valve 51 and a solenoid valve 7 in series. The oxygen output quantity control valve 51 is used for regulating the pressure and stabilizing the output of oxygen and the output quantity of oxygen when oxygen is output. The solenoid valve 7 controls the oxygen storage bucket 5 to conditionally output oxygen. After the oxygen tube 2 is fed with air for oxygen generation, the air channel 31 is closed via the solenoid valve 7 and simultaneously the exhaust channel 33 is opened, to realize oxygen storage and nitrogen exhaust. The structure is simple.

Figure 5:
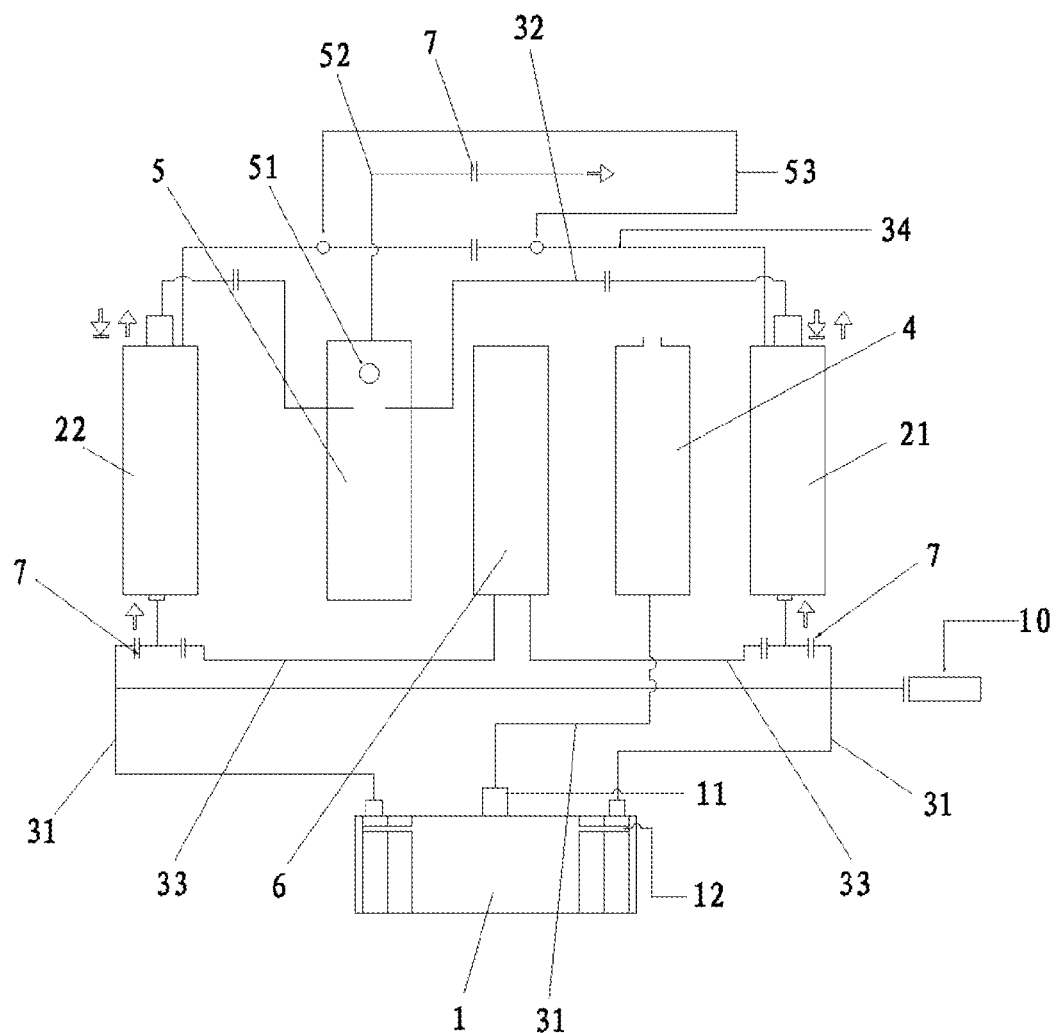
FIG. 5 is a schematic diagram of a portable oxygen generator in the invention.

As shown in FIG. 5, the molecular tube 2 in this embodiment comprises a first molecular tube 21 and a second molecular tube 22. The first molecular tube 21 and the second molecular tube 22 are communicated with each other through an oxygen complementation channel 34. The oxygen complementation channel 34 is connected with a solenoid valve 7. Oxygen complementation control valves 53 are disposed on two sides of the solenoid valve 7, respectively.

When the second molecular tube 22 performs exhaust, the oxygen complementation control valves 53 are opened. Then, the oxygen generated in the first molecular tube 21 may be conveyed to the upper part of the second molecular tube 22 via the oxygen complementation channel 34. This will help in exhausting nitrogen inside the second molecular tube 22 from the lower part thereof, so as to ensure that nitrogen inside the second molecular tube 22 is exhausted completely. Therefore, the processing efficiency of the second molecular tube 22 is improved and the prepared oxygen is high in purity. Similarly, the first molecular tube 21 is generating oxygen when the second molecular tube 22 is exhausting; and, the second molecular tube 22 is generating oxygen when the first molecular tube 21 is exhausting. When in service, it is just required to open the solenoid valves 7 connected with the first molecular tube 21 and the second molecular tube 22 successively, and then open the oxygen complementation control valves 53. Then, the conditional pipeline loop control is carried out by the solenoid valves 7 to ensure the uninterrupted working of the two molecular tubes 2. This facilitates circular oxygen generation and improves the processing efficiency of the oxygen generator.

Further, the oxygen complementation channel 34 is connected with an air flow control valve that is advantageous to regulate the demand of oxygen in the molecular tube 2 and adjust the complementation demand of oxygen in the molecular tube 2. Preferably, the molecular tube 2 further comprises a third molecular tube that is communicated with the first molecular tube 21 and the second molecular tube 22 via the oxygen complementation channel 34, to further improve the processing efficiency of the oxygen generator. Certainly, the molecular tube 2 may further comprise a fourth molecular tube and a fifth molecular tube. According to the demand of pure oxygen, a user may set the number of the molecular tubes 2 properly. Therefore, the invention has high use convenience and high practicability.

Figure 6:
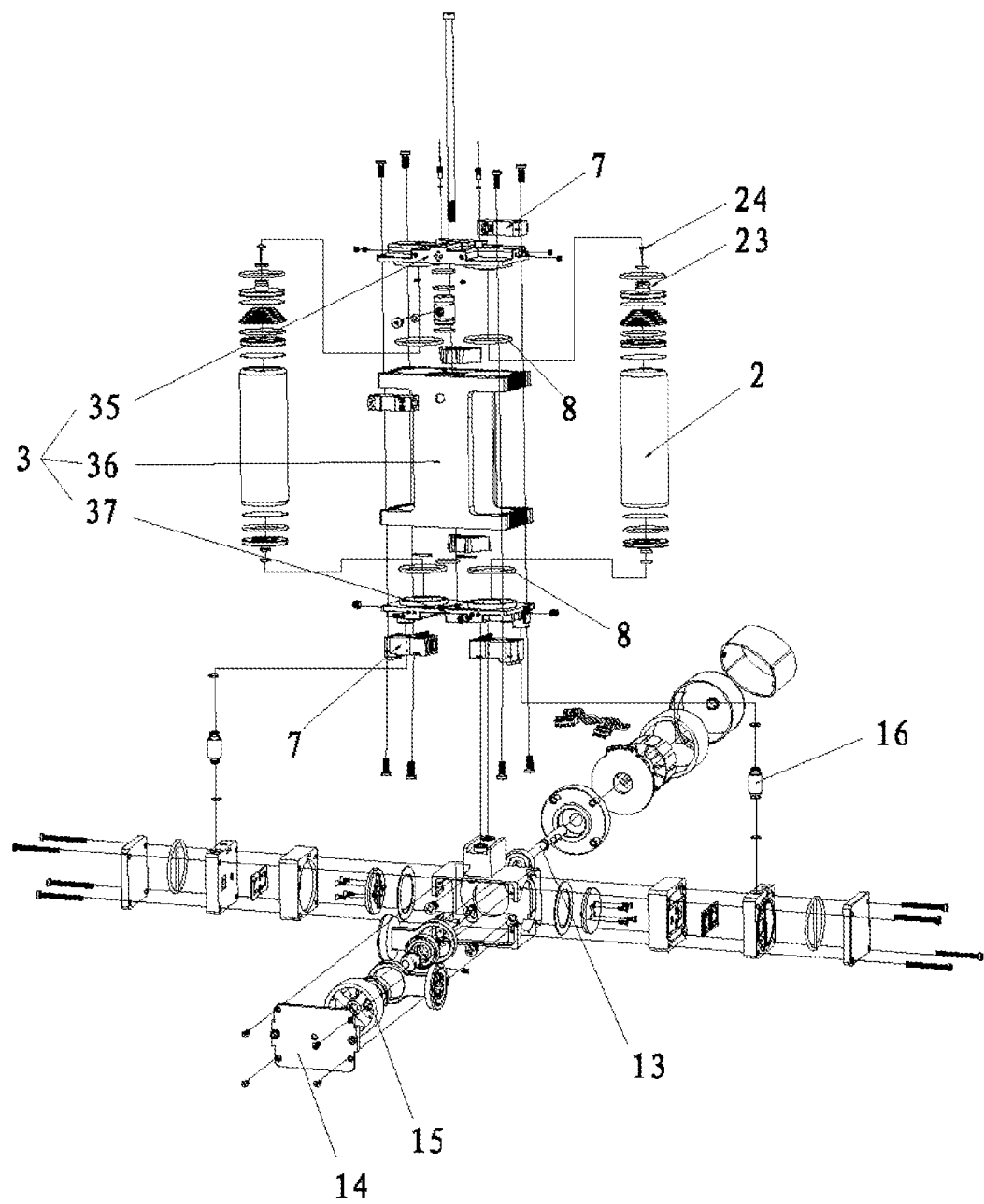
FIG. 6 is a decomposition structure diagram of a portable oxygen generator in the invention.

As shown in FIG. 6, the molecular seat 3 in this embodiment comprises an upper cover 35, a seat body 36 and a lower cover 37, which are disposed in turn from top to bottom. The seat body 36 is connected with the upper cover 35 and the lower cover 37 by bolts, respectively. Both the assembly and disassembly are convenient due to such a simple structure, and the processing efficiency is high. Specifically, the seat body 36 is provided with a long screw straightly from the lower cover 37 to the air pump 1. The seat body 36, the lower cover 37 and the air pump 1 are fixed by the screw. This ensures a compact assembly space of the molecular seat 3 and brings in high use reliability.

Further, the oxygen complementation channel 34 is disposed inside the upper cover 35. After the outside air from the upper cover 35 to the seat body 36 then to the lower cover 37 is filtered and cleaned by the air filter bucket 4, the air is compressed by the air pump 1 and then input from the lower part of the molecular tube 2. Then, the air is subjected to the material inside the molecular tube 2, so far, the oxygen is generated. The generated oxygen is guided by the oxygen complementation channel 34 on the upper cover 35 and then stored in the oxygen storage bucket 5. When a user needs oxygen, pure oxygen will be output from the oxygen storage bucket 5 timely for the user. The oxygen complementation channel 34 is disposed on the upper cover 35 so that the design of all airflow pipelines of the molecular seat 3 becomes more rational. As a result, the space utilization of the molecular seat 3 is improved. Therefore, the oxygen generator has high practicability.

Further, a closed rubber ring is provided between the upper cover 35 and the upper part of the molecular tube 2, so that the air tightness of the air outlet end of the molecular tube 2 is further strengthened. Therefore, the oxygen generator has high practicability.

As shown in FIG. 6, at the air outlet end of the molecular tube 2 in this embodiment, an oxygen outlet tip 23 is provided. An oxygen outlet tip slot fitted with the oxygen outlet tip 23 is provided on the upper cover 35. Therefore, it is ensured that the oxygen generated by the molecular tube 2 may be stored in the oxygen storage bucket 5 completely, and the leakage of oxygen from the air outlet end of the molecular tube 2 may be avoided effectively. Therefore, the oxygen generator has high air tightness.

Further, on the side where the upper cover 35 is connected with the seat body 36, a molecular tube frame 38 and a rubber sheath are provided for sealing the molecular tube 2 and preventing oxygen in the molecular tube 2 from leaking from the oxygen outlet tip 23.

As shown in FIG. 6, an umbrella-shaped non-return reflux device 24 is disposed on the top of the oxygen outlet tip 23 in this embodiment. The arrangement of the umbrella-shaped non-return reflux device 24 makes the oxygen generated in the molecular tube 2 enter the oxygen storage bucket 5 smoothly and not return at the upper part of the molecular tube 2. This avoids the reflux of oxygen and also prevents oxygen communication between the molecular tubes 2. Therefore, the oxygen generator has high use safety and practicability.

Figure 2:
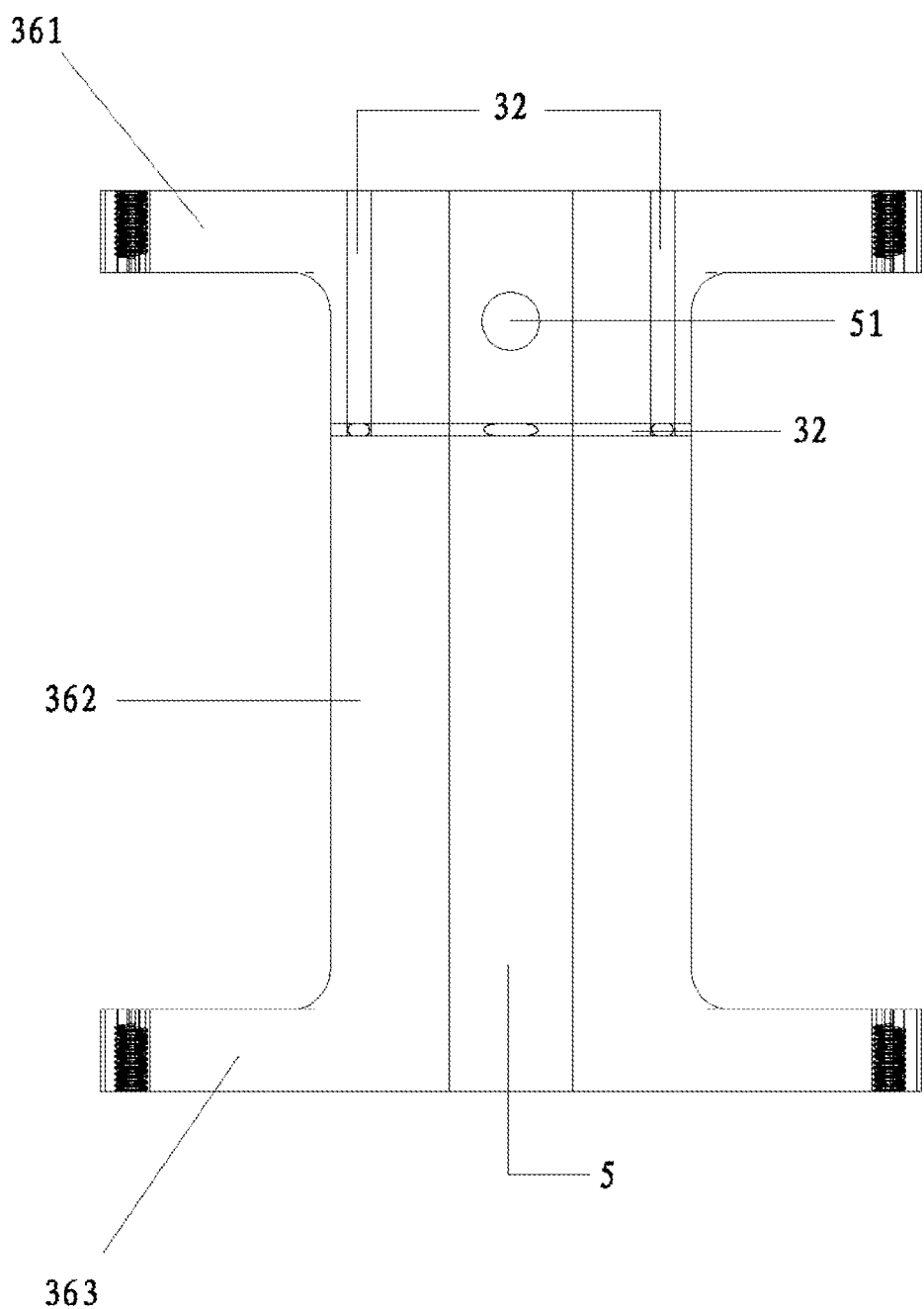
FIG. 2 is a side structure diagram of a seat body of a molecular seat of a portable oxygen generator in the invention.
Figure 3:
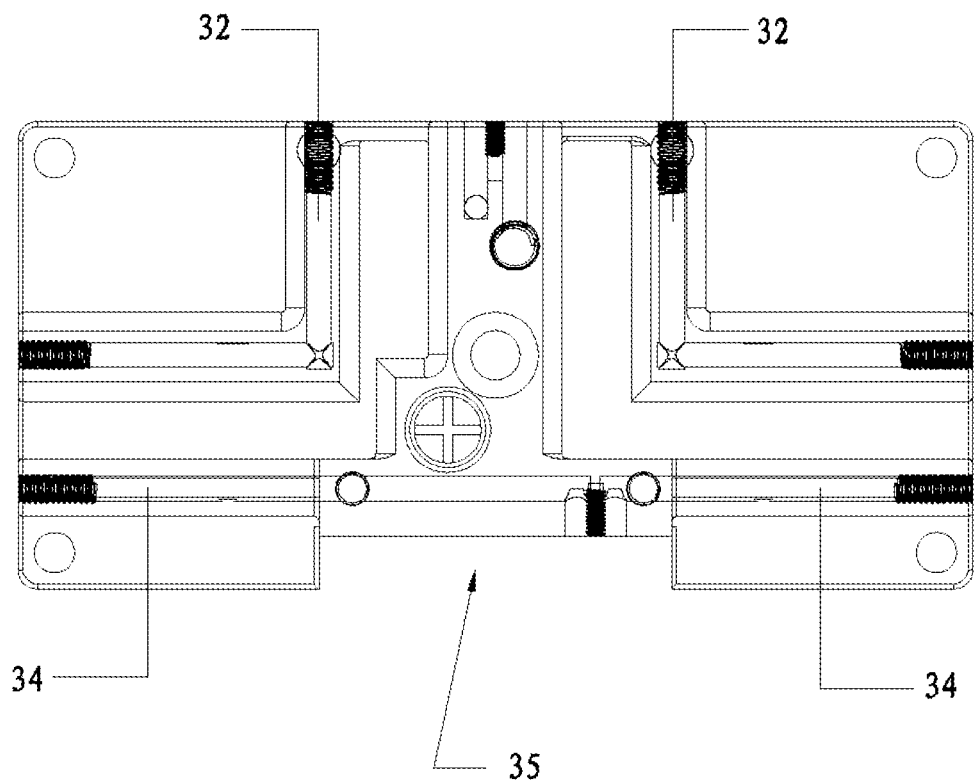
FIG. 3 is a front structure diagram of an upper cover of a molecular seat of a portable oxygen generator in the invention.
Figure 4:
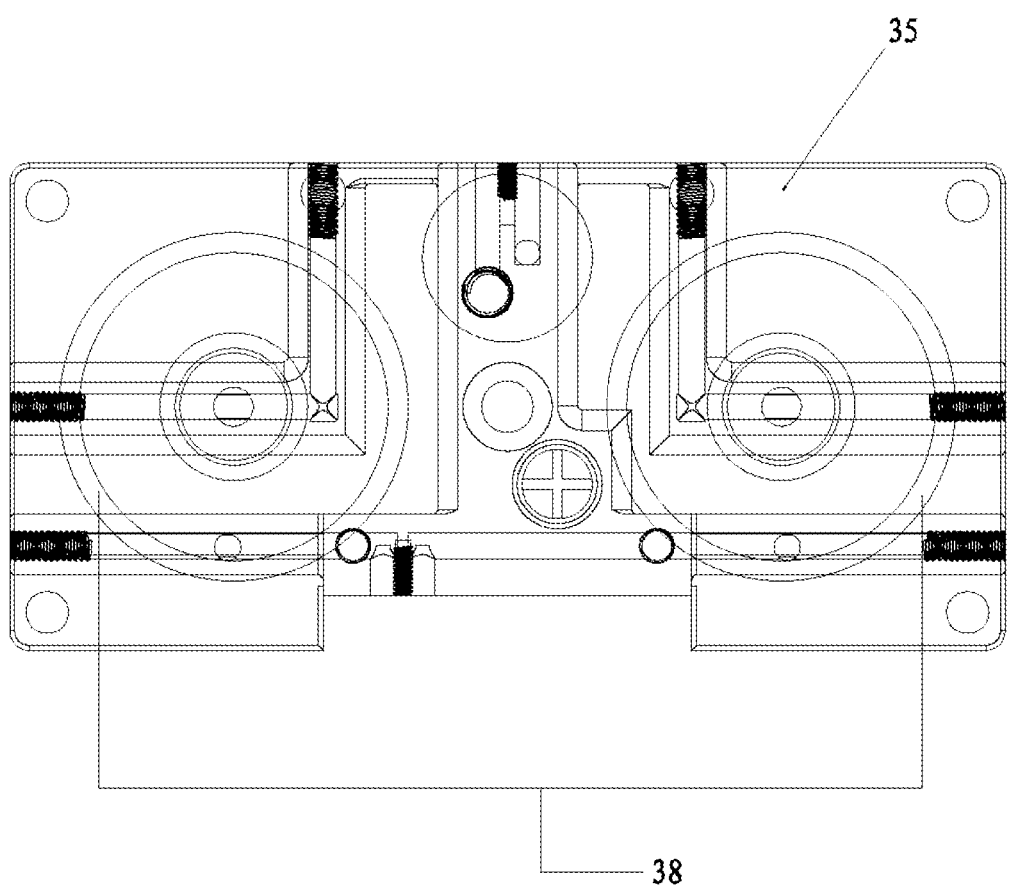
FIG. 4 is a rear structure diagram of an upper cover of a molecular seat of a portable oxygen generator in the invention.

As shown in FIG. 2, the seat body 36 in this embodiment comprises a top 361, a middle part 362 and a bottom 363, which are integrated together. A side face of the seat body 36 is I-shaped. Through holes are disposed at two ends of the top 361, respectively. Counter bores are disposed at two ends of the bottom 363, respectively. The counter bores are right below the through holes. When the molecular tube 2 is assembled, the molecular tube 2 can be pasted on the side wall of the middle part 363 of the seat body 36 stably when directly inserted along the through holes. Therefore, the oxygen generator has simple structure and is convenient for assembling and disassembling.

As shown in FIG. 6, a motor connector 16 is disposed at the air outlet end of the air pump 1 in this embodiment. A concave-convex slot joint is disposed in a position where the lower cover 37 directly faces the air inlet end of the molecular tube 2. The concave-convex slot joint is connected with the motor connector 16 in a way of muff-coupling. When in service, the air is compressed by the air pump 1, then passed through the lower cover 37 via the motor connector 16, and finally input from the lower part of the molecular tube 2 for oxygen generation. Therefore, the oxygen generator has good air tightness.

Further, a closed rubber ring is provided between the lower cover 37 and the lower part of the molecular tube 2, so that the air tightness of the molecular tube 2 is further enhanced. Therefore, the oxygen generator has high practicability.

As shown in FIG. 1, multiple cooling fins 9, arrayed at intervals, are disposed on the outer wall of the molecular seat 3 in this embodiment. The arrangement of the cooling fins 9 is advantageous to heat dissipation of airflow in the air pump 1 and of airflow flowing through the molecular seat 3. This prolongs the service life of the oxygen generator. Therefore, the oxygen generator has simple structure and high use reliability.

As shown in FIG. 5, the air channel 31 between the molecular tube 2 in this embodiment and the air pump 1 is connected with an over-pressure protection device 10. When the air channel 31 is blocked, the pressure control valve of the over-pressure protection device 10 will regulate the pressure to a certain safe pressure automatically to control the air channel 31 to exhaust automatically. Therefore, the oxygen generator has high use safety.

As shown in FIG. 5, an air suction tip 11 is disposed at the air inlet end of the air pump 1 in this embodiment. A suction silencing channel 12 is disposed between an air cylinder and an air reservoir of the air pump 1. The rotating shaft 13 of the air pump 1 is provided with a safety cover 14. The arrangement of the air suction tip 11 assists in sucking the dehumidified and filtered air into the air pump 1 to be conveyed to the molecular tube 2 after compressed by the air pump. The suction silencing channel 12 is advantageous to reduction of noise caused by the running of the air pump 1. The safety cover 14 ensures that the air pump 1 is free from the disturbance of other matters when it runs. Therefore, the oxygen generator has high use safety and reliability.

Further, counterweight copper 15 is sleeved outside of the rotating shaft 13 of the air pump 1, thereby improving the pumping inertia of the air pump 1, reducing the loss of the air pump 1 effectively and prolonging the service life of the air pump 1.

Of course, the above contents just describe the preferred embodiments of the invention. All equivalent changes or modifications made according to the structure, characteristics and principle defined in the patent scope of the invention shall fall into the patent scope of the invention.

What is claimed is:
1. A portable oxygen generator, comprising:
   an air pump;
   two or more molecular tubes;
   a molecular seat comprising molecular tube grooves, wherein the two or more molecular tubes are detachably fixed on a side wall of the molecular seat in the molecu- lar tube grooves and the air pump being is disposed at a lower part of the molecular seat;

an air filter bucket with an air inlet connected to outside air;

an oxygen storage bucket;

an exhaust silencing bucket wherein the air filter bucket, oxygen storage bucket, and exhaust silencing bucket are all disposed inside the molecular seat;

an air channel;

an oxygen channel; and an exhaust channel wherein the two or more molecular tubes and the air channel, oxygen channel, and exhaust channel are all disposed inside the molecular seat, the air channel being respectively communicated with the air filter bucket, the air pump and the two or more molecular tubes, the oxygen channel being respectively communicated with the two or more molecular tubes and the oxygen storage bucket, the exhaust channel being respectively communicated with the two or more molecular tubes and the exhaust silencing bucket, the air channel, the oxygen channel and the exhaust channel being respectively connected with a solenoid valve.

2. The portable oxygen generator according to claim 1, wherein the seat body comprises a top, a middle part and a bottom, which are integrated together, a side face of the seat body being I-shaped, through holes being respectively disposed at two ends of the top, counter bores being respectively disposed at two ends of the bottom, the counter bores being right below the through holes.

3. The portable oxygen generator according to claim 1, wherein the molecular tube comprises a first molecular tube and a second molecular tube, the first molecular tube and the second molecular tube being communicated with each other through an oxygen complementation channel, the oxygen complementation channel being connected with a solenoid valve, oxygen complementation control valves being respectively disposed on two sides of the solenoid valve.

4. The portable oxygen generator according to claim 3, wherein the seat body comprises a top, a middle part and a bottom, which are integrated together, a side face of the seat body being I-shaped, through holes being respectively disposed at two ends of the top, counter bores being respectively disposed at two ends of the bottom, the counter bores being right below the through holes.

5. The portable oxygen generator according to claim 3, wherein the molecular seat comprises an upper cover, a seat body and a lower cover, which are disposed in turn from top to bottom, the seat body being respectively connected with the upper cover and the lower cover by bolts.

6. The portable oxygen generator according to claim 5, wherein the seat body comprises a top, a middle part and a bottom, which are integrated together, a side face of the seat body being I-shaped, through holes being respectively disposed at two ends of the top, counter bores being respectively disposed at two ends of the bottom, the counter bores being right below the through holes.

7. The portable oxygen generator according to claim 5, wherein an oxygen outlet tip is disposed at the air outlet end of the molecular tube, and a groove for the oxygen outlet tip fitted with the oxygen outlet tip in mounting is disposed on the upper cover.

8. The portable oxygen generator according to claim 7, wherein the seat body comprises a top, a middle part and a bottom, which are integrated together, a side face of the seat body being I-shaped, through holes being respectively disposed at two ends of the top, counter bores being respectively disposed at two ends of the bottom, the counter bores being right below the through holes.

9. The portable oxygen generator according to claim 7, wherein an umbrella-shaped non-return reflux device is disposed on the top of the oxygen outlet tip.

10. The portable oxygen generator according to claim 9, wherein the seat body comprises a top, a middle part and a bottom, which are integrated together, a side face of the seat body being I-shaped, through holes being respectively disposed at two ends of the top, counter bores being respectively disposed at two ends of the bottom, the counter bores being right below the through holes.

11. The portable oxygen generator according to claim 5, wherein a motor connector is disposed at the air outlet end of the air pump, a concave-convex slot joint is disposed in a position where the lower cover directly faces the air inlet end of the molecular tube, and the concave-convex slot joint is connected with the motor in a way of muff-coupling.

12. The portable oxygen generator according to claim 1, wherein multiple cooling fins, arrayed at intervals, are disposed on the outer wall of the molecular seat.

13. The portable oxygen generator according to claim 1, wherein the air channel between the molecular tube and the air pump is connected with an over-pressure protection device.

14. The portable oxygen generator according to claim 1, wherein an air suction tip is disposed at the air inlet end of the air pump, a suction silencing channel is disposed between an air cylinder and an air reservoir of the air pump, and a rotating shaft of the air pump is provided with a safety cover.

* * * * *